United States Patent
Atiyeh et al.

(10) Patent No.: US 10,053,711 B2
(45) Date of Patent: Aug. 21, 2018

(54) METHOD IMPROVING PRODUCER GAS FERMENTATION

(71) Applicants: THE BOARD OF REGENTS FOR OKLAHOMA STATE UNIVERSITY, Stillwater, OK (US); BRIGHAM YOUNG UNIVERSITY, Provo, UT (US)

(72) Inventors: Hasan K. Atiyeh, Stillwater, OK (US); Randy S. Lewis, Provo, UT (US); John Randall Phillips, Middletown, DE (US); Raymond L. Huhnke, Stillwater, OK (US)

(73) Assignees: THE BOARD OF REGENTS FOR OKLAHOMA STATE UNIVERSITY, Stillwater, OK (US); BRIGHAM YOUNG UNIVERSITY, Provo, UT (US)

( * ) Notice: Subject to any disclaimer, the term of this patent is extended or adjusted under 35 U.S.C. 154(b) by 114 days.

(21) Appl. No.: 14/909,578

(22) PCT Filed: Aug. 4, 2014

(86) PCT No.: PCT/US2014/049608
§ 371 (c)(1),
(2) Date: Feb. 2, 2016

(87) PCT Pub. No.: WO2015/017857
PCT Pub. Date: Feb. 5, 2015

(65) Prior Publication Data
US 2016/0215303 A1 Jul. 28, 2016

Related U.S. Application Data

(60) Provisional application No. 61/861,756, filed on Aug. 2, 2013.

(51) Int. Cl.
*C12P 7/06* (2006.01)
*C12N 1/20* (2006.01)
*C12N 1/38* (2006.01)

(52) U.S. Cl.
CPC ................ *C12P 7/065* (2013.01); *C12N 1/20* (2013.01); *C12N 1/38* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 3,706,812 A | 12/1972 | Derosset et al. | |
| 6,979,402 B1 | 12/2005 | Sprague et al. | |
| 8,507,228 B2 * | 8/2013 | Simpson | C12M 21/12 |
| | | | 210/601 |
| 8,980,596 B2 * | 3/2015 | Schultz | C12P 7/06 |
| | | | 435/158 |
| 9,469,860 B2 | 10/2016 | Enzien et al. | |
| 9,617,509 B2 | 4/2017 | Li et al. | |
| 9,663,802 B2 | 5/2017 | Hickey | |
| 9,701,987 B2 | 7/2017 | Smart et al. | |
| 2010/0203606 A1 | 8/2010 | Huhnke et al. | |
| 2010/0323417 A1 * | 12/2010 | Simpson | C12M 21/12 |
| | | | 435/157 |
| 2011/0108762 A1 | 5/2011 | Allais et al. | |
| 2013/0316412 A1 | 11/2013 | Schultz et al. | |
| 2016/0338380 A1 | 11/2016 | Simpson et al. | |
| 2017/0218404 A1 | 8/2017 | Simpson et al. | |

FOREIGN PATENT DOCUMENTS

WO WO 2009/141361 * 11/2009
WO 2012026833 A1 3/2012

OTHER PUBLICATIONS

PCT/US2014/049608 International Search Report and Written Opinion.
PCT/US2014/049608, filed Aug. 4, 2014, International Preliminary Report on Patentability.

* cited by examiner

*Primary Examiner* — Yong D Pak
(74) *Attorney, Agent, or Firm* — Crowe & Dunlevy; Terry L. Watt

(57) ABSTRACT

Providing a microbial catalyst in a reaction broth, providing an adsorptive solid into the reaction broth, providing a producer gas into the reaction broth, and obtaining a fermentation product from the reaction broth resulting from activity of the microbial catalyst in the presence of the adsorptive solid.

17 Claims, 4 Drawing Sheets

METHOD IMPROVING PRODUCER GAS FERMENTATION

CROSS REFERENCE TO RELATED APPLICATION

This application claims the benefit of U.S. Provisional Application No. 61/861,756 filed Aug. 2, 2013, herein incorporated by reference in its entirety for all purposes.

STATEMENT REGARDING FEDERAL SPONSORED RESEARCH OR DEVELOPMENT

This invention was made with U.S. Government support under USDA/NIFA Grant No. 2009-34447-19951 and USDA/NIFA Grant No. 2010-34447-20772 awarded by the Department of Agriculture and under DOT Grant No. DTOS59-07-G-00053 awarded by the Department of Transportation. The Government has certain rights in this invention.

FIELD OF THE INVENTION

The present invention relates generally to the field of gas fermentation and, more particularly, to improving gas fermentation processes by the use of additives.

DETAILED DESCRIPTION OF THE PREFERRED EMBODIMENTS

Figure 1:
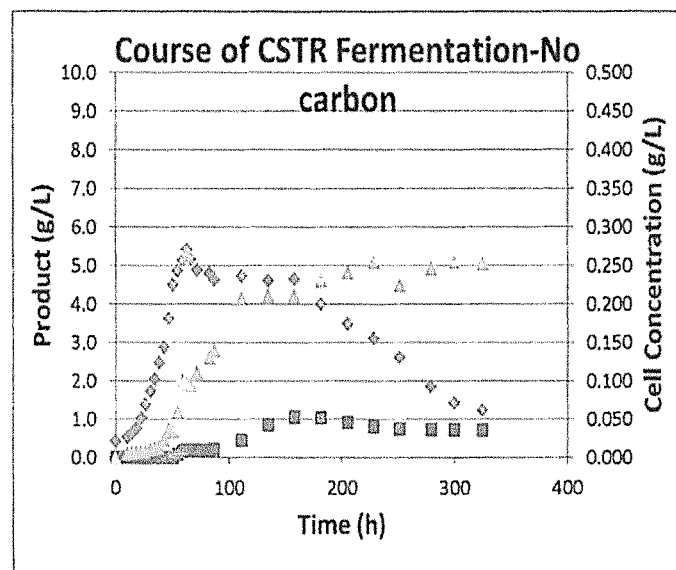
FIG. 1 is a graph of accumulated products for batch fermentation of syngas in continuously stirred tank reactors (CSTR) without activated carbon for (▲) acetic acid, (■) ethanol, (♦) cell mass.

Hybrid thermochemical-biochemical technology, such as gasification-fermentation, has the potential to increase alcohol yield by more than 35% compared to the saccharification-fermentation process due to the utilization of all components of the biomass (cellulose, hemicellulose, and lignin). In gasification, biomass is converted into syngas/producer gas, primarily consisting of CO, $CO_2$, and $H_2$. Syngas/producer gas fermentation involves complex biochemical reactions to convert $H_2$, CO and/or $CO_2$ into liquid fuels using microbial catalysts such as *Clostridium ljungdahlii, Clostridium carboxidivorans, Clostridium ragsdalei, Alkalibaculum bacchi* (Liou et al., 2005; Liu et al., 2012; Maddipati et al., 2011; Phillips et al., 1994; Tanner et al., 2008; Wilkins and Atiyeh, 2011). Ethanol and acetic acid are the main products from the above microorganisms. Additional products, such as butanol, have also been identified as products of syngas/producer gas fermentation (Maddipati et al., 2011; Munasinghe and Khanal, 2010). Syngas/producer gas fermentation occurs via the "Wood-Ljungdahl" pathway in which $CO_2$ and/or CO are used as the carbon substrates for alcohol, organic acid, and cell formation. Reducing equivalents (i.e., electrons) are produced through either consumption of $H_2$ via the hydrogenase enzyme or by reduction of CO to $CO_2$ via the carbon monoxide dehydrogenase (CODH) enzyme.

Gasification-fermentation of biomass to ethanol is still an emerging technology. In various embodiments, the present disclosure advances the field by providing for gasification of switchgrass followed by the fermentation of the resulting biomass-generated syngas/producer gas to fuel ethanol using novel microbial catalysts and various bioreactor designs. Initial fermentation analysis, using either biomass-generated syngas/producer gas or "clean" syngas/producer gas made from compressed gases, involved the use of bubble column reactors or continuously stirred tank reactors (CSTR) with *Clostridium carboxidivorans* and *Clostridium P11* (Hurst and Lewis, 2010; Maddipati et al., 2011). In addition to the above findings, it has been observed that mass transfer of CO, $CO_2$, and $H_2$ to the cells can limit the rates of cell growth and ethanol to acetic acid production ratio (Hurst and Lewis, 2010).

*Clostridium ragsdalei, C. carboxidivorans, C. ljungdahlii, Alkalibaculum bacchi* and other autotrophic acetogenic bacteria can convert CO, $CO_2$ and $H_2$ in syngas/producer gas to alcohols, organic acids and other chemicals that are used in transportation and commodity industries. The production of these products via syngas/producer gas fermentation relies on transfer of the CO, $CO_2$ and $H_2$ to bacteria cells in an aqueous medium at rates that match the kinetic capability to process the gas. If too much CO accumulates in the fermentation broth, the cells are inhibited and convert the gas slowly. If too little CO and $H_2$ accumulate in the broth, the product will be acetic acid, not ethanol, and rates will be limited by the transfer rate of the gas. Optimum fermentation conditions are achieved when gas supply matches the kinetic capability of active microbial cells.

In various embodiments of the present disclosure, fine powdered activated carbon is added to a fermentation broth to alter the mass transfer of the gas to the bacterium used. The activated carbon (Carbon Resources CR1250CP, with a mean particle size of 7 microns) used in this embodiment is commercially available. However, other types and sources of activated carbon with a mean particle sizes averaging 7 microns to granular or larger sizes can be used with this embodiment. The activated carbon can be produced from carbonaceous sources such as wood, coal, coconut husk and petroleum. Different precursors, carbonizations and activation procedures have been used to produce a wide variety of activated carbons for different applications. Additionally, other adsorptive or catalytic solids such as zeolites, clay, char or activated char can be used in this embodiment.

The addition of activated carbon sustained the bacterial cells' activity, prolonged the fermentation process and resulted in a very high specificity for and high concentration of ethanol produced. The increase in production of ethanol and fermentation stability was attributable to the effect of carbon in altering the mass transfer and presumably in retaining nutrients to sustain the fermentation activity. This is consistent with the mechanisms of activated carbon use, particularly adsorption of organic compounds.

In one example, *Clostridium ragsdalei*, a common acetogen was used for testing gas fermentation in 250-ml serum bottles. The preliminary results showed no increase in CO or $H_2$ transfer rate; however, adding carbon to the medium appeared to prolong fermentation activity. The gas used in the experiment was a commercial gas mixture made of CO, $H_2$, $CO_2$ and $N_2$ that simulated the producer gas made from gasifying switchgrass, or a mix that simulated coal derived syngas.

Figure 2:
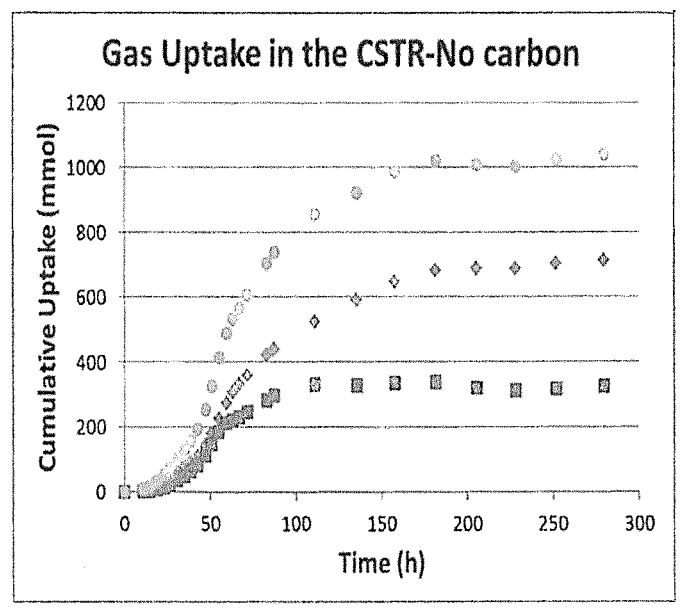
FIG. 2 is a graph of cumulative gas uptake in CSTR batch fermentation without activated carbon for (■) H2, (♦) CO, (●) CO+$H_2$.
Figure 3:
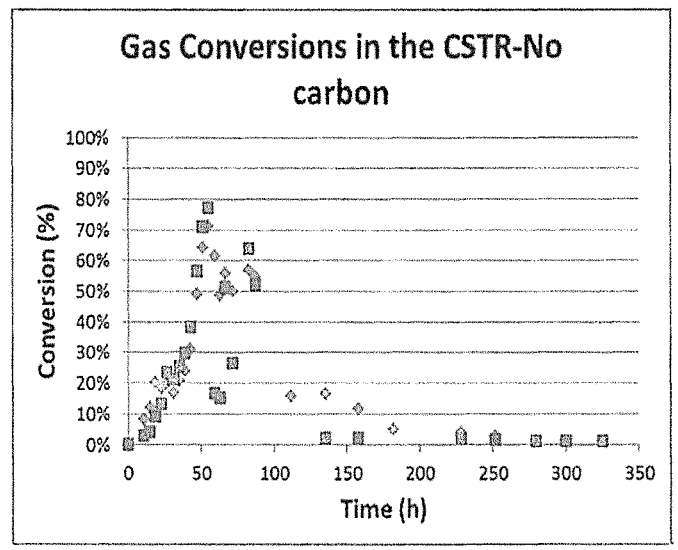
FIG. 3 is a graph of conversion efficiencies for the substrate gases in CSTR batch fermentation without activated carbon for (■) $H_2$, (♦) CO.
Figure 4:
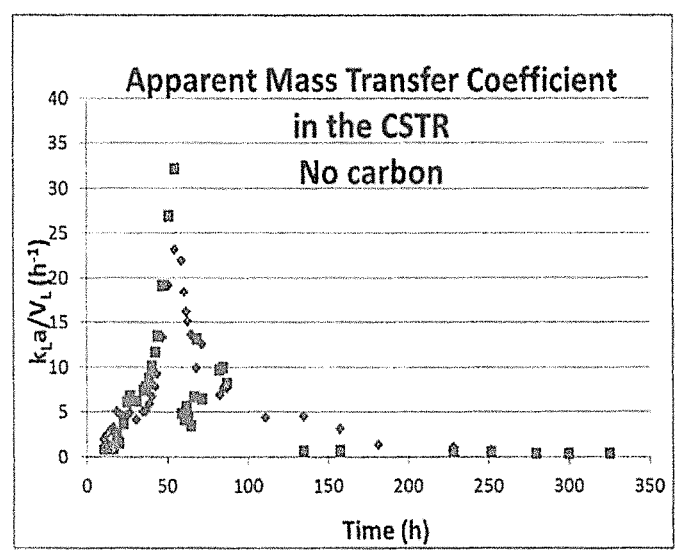
FIG. 4 is a graph of mass transfer coefficient ($k_L a/V_L$) in CSTR batch fermentation without activated carbon for (■) $H_2$, (♦) CO.

In another example, gas fermentations were performed in a 3-L CSTR containing a typical fermentation medium. This process was performed both with and without addition of very fine activated carbon. In the present example, the carbon used was Carbon Resources CR1250CP, with a mean particle size of 7 microns. The fermentations without activated carbon in the 3-L CSTR were active for a short period (about 122 h) and produced mostly acetic acid (about 6.0 g/L) with much lower production of ethanol (less than 1.0 g/L) as shown in FIG. 1. The cell concentration in the fermentation medium sharply decreased after 158 h with no more ethanol production. The cumulative gas (CO and $H_2$) uptake increased in the first 181 h, after which gas consumption stopped (FIG. 2). The decreasing gas uptake rate by the microorganism is due to the reduced cell activity and inhibition by CO of the hydrogenase enzyme. This is clear by the complete inhibition of cells to uptake $H_2$ after 110 h. Conversion efficiencies of CO and $H_2$ of over 50% were only attained for 40 h of fermentation between 47 and 87 h (FIG. 3). Additionally, the apparent mass transfer coefficient for CO ($k_{L,CO}a/V_L$) was between 15 and 32 $h^{-1}$ for only 15 h between 47 h and 62 h of fermentation (FIG. 4). The initial increase in the mass transfer coefficient of both CO and $H_2$ was due to cell growth. However, the mass transfer rate decreased after about 50 h due to combined effect of reduced cells activity and possible inhibition by accumulated CO.

Figure 5:
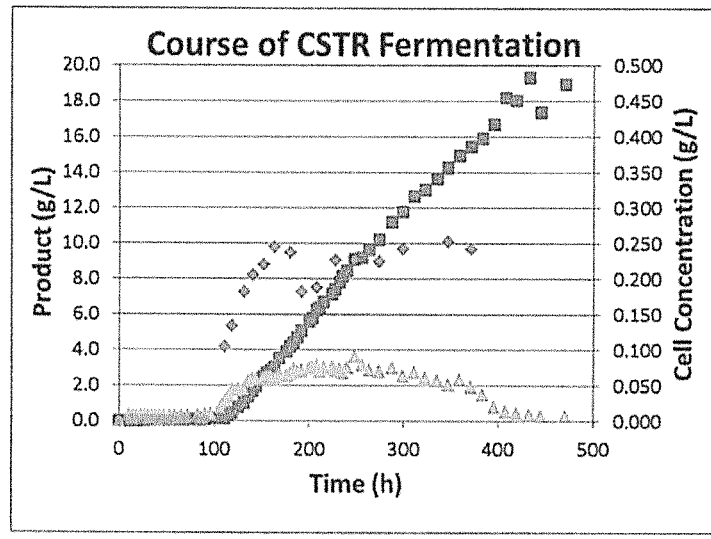
FIG. 5 is a graph of accumulated products for batch fermentation of syngas in CSTR batch fermentation with activated carbon for (▲) acetic acid, (■) ethanol, (♦) cell mass.

As shown in FIG. 5, batch fermentation with added carbon first exhibited a lag phase with low fermentation activity, probably associated with activity of the inoculum. Then, it transitioned to a prolonged fermentation with up to 300 hours of nearly constant conversion of CO and $H_2$ into ethanol (19 g/L) with a small production of acetic acid (up to 3.0 g/L at 250 h with a final concentration less than 1.0 g/L). The fermentation with activated carbon showed that cell activity was sustained for longer time (FIG. 5) compared to the no carbon fermentation (FIG. 1).

The cell concentration in the medium without carbon was measured from a 1 mL subsample as optical density (OD) at 660 nm wavelength with a 1 cm light path using a UV-vis spectrophotometer. A direct measurement of cell concentration in fermentations with activated carbon was not possible because the carbon particles interfere with the OD measurement. Therefore, we indirectly measured cell concentration using a modified Bradford protein analysis method; estimated cell concentration (FIG. 5) was similar to that seen in fermentation without carbon (FIG. 1).

Figure 6:
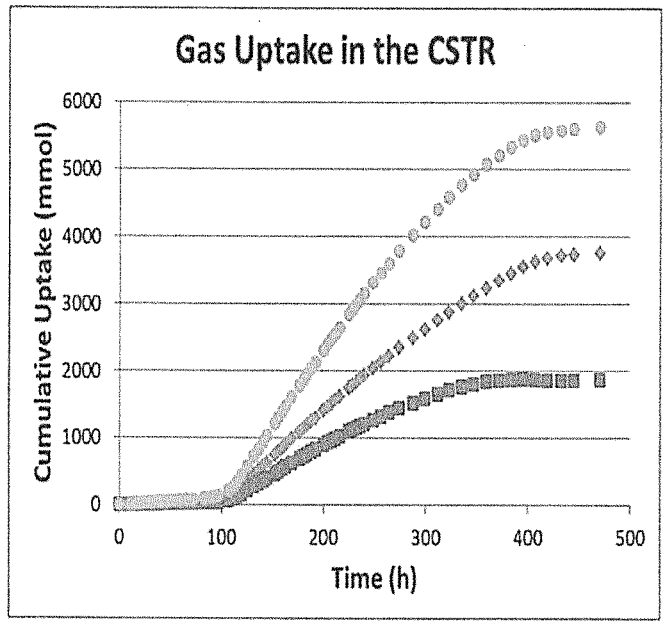
FIG. 6 is a graph of cumulative gas uptake in CSTR batch fermentation with activated carbon for (■) H2, (♦) CO, (●) CO+$H_2$.
Figure 7:
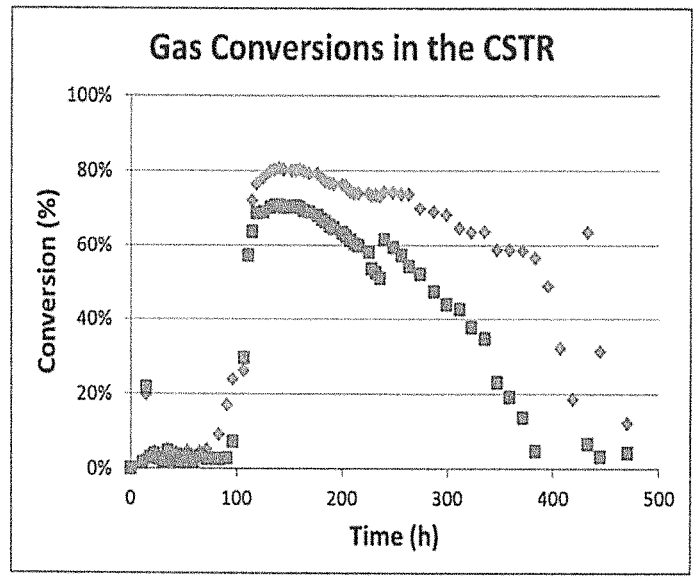
FIG. 7 is a graph of conversion efficiencies for the substrate gases in CSTR batch fermentation with activated carbon for (■) $H_2$, (♦) CO.
Figure 8:
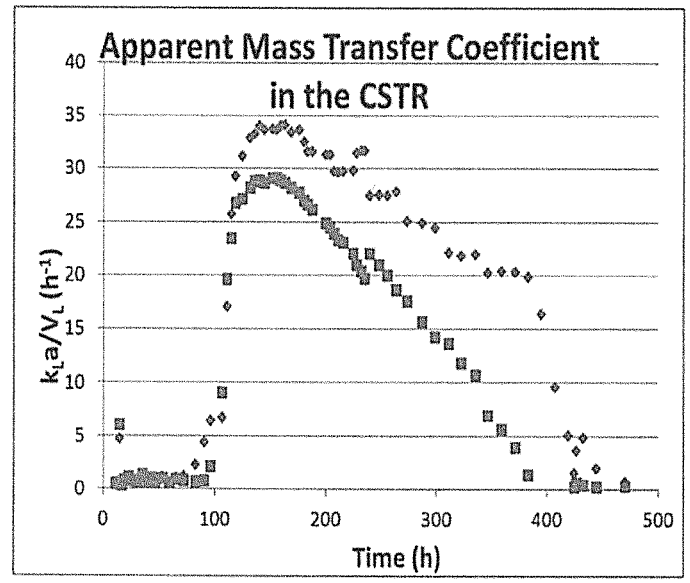
FIG. 8 is a graph of mass transfer coefficient ($k_L a/V_L$) in CSTR batch fermentation with activated carbon (■) $H_2$, (♦) CO.

The addition of activated carbon to the fermentation medium resulted in a conversion of over 5600 mmol of CO plus $H_2$ by *C. ragsdalei* in 470 hours (FIG. 6). This is over fivefold higher than the gas consumed without the carbon (FIG. 2). The maximum conversion efficiencies of CO and $H_2$ with the addition of activated carbon to the medium were 80% and 70%, respectively (FIG. 7). CO and $H_2$ conversion efficiencies in the medium with activated carbon were above 50% for over 160 h from 110 h to 274 h of fermentation. In addition, the maximum apparent mass transfer coefficients for CO and $H_2$ in the medium with activated carbon were 34 $H^{-1}$ and 29 $H^{-1}$, respectively (FIG. 8). The apparent mass transfer coefficient for CO ($k_{L,CO}a/V_L$) in the medium with carbon was above 15 $h^{-1}$ for over 176 h compared to a period of only 15 h in the medium without carbon. The rate of gas transfer in fermentations with and without activated carbon was controlled by changing the agitator speed and/or gas flow rate.

The maximum uptake rates of $H_2$, CO and their sum were similar with or without carbon. However, the uptake rates were sustained in the fermentation with carbon.

The operational stability and selectivity of *Clostridium ragsdalei* for ethanol as the preferred product provided by the activated carbon is needed for biofuel production. Stability and selectivity at high production rates are key goals of any potential commercial biofuel process. High conservation of energy in the initial resource into the product is an additional key. The operation of the syngas/producer gas fermentation with activated carbon exhibits higher stability, selectivity and energy conservation than any previously reported results.

Although the present examples involve the use of *C. ragsdalei*, the system and methods of the present disclosure should be applicable and effective with any autotrophic acetogenic microbial culture that has solventogenic potential, and for other gas fermentation processes.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art.

What is claimed is:

1. A method comprising:
   providing a microbial catalyst in a fermentation broth, said microbial catalyst comprising *Clostridium ragsdalei;*
   providing activated carbon into the fermentation broth within the bioreactor;
   providing a producer gas comprising CO into the fermentation broth; and
   obtaining a fermentation product comprising ethanol from the fermentation resulting from activity of the microbial catalyst in the presence of the activated carbon.

2. The method of claim 1, wherein providing activated carbon into the fermentation broth further comprises providing powdered activated carbon into the fermentation broth.

3. The method of claim 2, wherein the powdered activated carbon comprises particles having a mean size averaging 7 microns in size.

4. The method of claim 1, wherein providing said producer gas into the fermentation broth further comprises providing at least one of $H_2$ and $CO_2$ plus $H_2$ into the fermentation broth.

5. A method comprising:
   providing a reaction broth containing activated carbon and a microbial catalyst in a reaction vessel, wherein said microbial catalyst comprises *Clostridium ragsdalei*; and
   producing a fermentation product comprising ethanol from said reaction broth and a producer gas comprising CO introduced into the reaction vessel, the fermentation product resulting from fermentation by the microbial catalyst in the presence of the activated carbon.

6. The method of claim 5, wherein providing a reaction broth containing activated carbon further comprises providing a reaction broth containing powdered activated carbon.

7. The method of claim 6, wherein the powdered activated carbon comprises particles having a mean averaging 7 microns in size.

8. The method of claim 5, wherein providing said producer gas into the reaction broth further comprises providing at least one of $H_2$ and $CO_2$ plus $H_2$ into the reaction broth.

9. A method comprising:
gasifying a biomass feedstock to produce a syngas
said syngas comprised of CO;
providing a reaction medium containing powdered activated carbon with a mean particles size of less than 7 microns; and
fermenting said reaction medium in the presence of said syngas using *Clostridium ragsdalei* to produce ethanol.

10. A method compromising:
providing a syngas comprised of CO;
providing a reaction broth containing suspended catalytic solids therein, said suspended catalytic solids comprising activated carbon;
fermenting said reaction broth in the presence of said syngas using an autotrophic acetogenic microbe catalyst to produce a quantity of ethanol, wherein said autotrophic acetogenic microbe catalyst comprises *Clostridium ragsdalei*.

11. The method of claim 10, wherein said suspended catalytic solids comprise powdered activated carbon with a mean particles size of less than 7 microns.

12. The method of claim 10, wherein said autotrophic acetogenic microbe comprises at least one of *Clostridium ragsdalei, C. carboxidivorans, C. ljungdahlii*, and *Alkalibaculum bacchi*.

13. The method of claim 10, wherein the step of providing a syngas comprises gasifying a biomass to produce said syngas.

14. A method compromising:
providing a syngas comprised of CO;
providing a reaction broth containing suspended solids therein, said suspended solids comprising activated carbon;
fermenting said reaction broth in the presence of said syngas using an autotrophic acetogenic microbe catalyst to produce a quantity of ethanol, wherein said autotrophic acetogenic microbe catalyst comprises *Clostridium ragsdalei*.

15. The method of claim 14, wherein said suspended solids comprise powdered activated carbon with a mean particles size of less than 7 microns.

16. The method of claim 14, wherein said suspended solids comprise at least one of powered zeolites, clay, char, activated char, carbon and activated carbon.

17. The method of claim 10, wherein providing syngas into the fermentation broth further comprises providing at least one of $H_2$ and $CO_2$, plus $H_2$ into the fermentation broth.

* * * * *